United States Patent [19]

Roller

[11] Patent Number: 4,857,306

[45] Date of Patent: Aug. 15, 1989

[54] COSMETIC COMPOSITION, PARTICULARLY FOR DECORATIVE APPLICATIONS

[76] Inventor: Joachim Roller, Blumenstrasse 7A, Neustetten 1, Fed. Rep. of Germany, D-7401

[21] Appl. No.: 45,132

[22] PCT Filed: Aug. 29, 1986

[86] PCT No.: PCT/DE86/00347

§ 371 Date: Jun. 15, 1987

§ 102(e) Date: Jun. 15, 1987

[87] PCT Pub. No.: WO87/01278

PCT Pub. Date: Mar. 12, 1987

[30] Foreign Application Priority Data

Aug. 29, 1985 [DE] Fed. Rep. of Germany ....... 3530902

[51] Int. Cl.$^4$ .................. A61K 7/021; A61K 7/027; A61K 7/031; A61K 7/032

[52] U.S. Cl. ........................ 424/63; 424/61; 424/64; 424/69; 514/844; 514/845; 106/401; 106/504

[58] Field of Search .............. 424/61, 63, 64, 69; 106/288 B, 307, 316, 401, 415, 450, 499, 504

[56] References Cited

U.S. PATENT DOCUMENTS 4,482,538 11/1984 Davies .................................. 424/61
4,640,943 2/1987 Meguro et al. ................... 424/69 X

FOREIGN PATENT DOCUMENTS 198608 9/1987 Japan.

*Primary Examiner*—Ellis P. Robinson
*Assistant Examiner*—Susan S. Rucker
*Attorney, Agent, or Firm*—Bachman & LaPointe

[57] ABSTRACT

The invention relates to a cosmetic composition, particularly for decorative applications, with a proportional content of a liquid, highly viscous or solid, dermatologically compatible carrier material and a pure powder of precious stones or precious stone mixtures.

11 Claims, No Drawings

COSMETIC COMPOSITION, PARTICULARLY FOR DECORATIVE APPLICATIONS

The present invention relates to a cosmetic composition, particularly for decorative applications. Decorative cosmetics mostly involve carrier materials compounded with dyes or pigments which are intended to place coloured accents in the wearers' faces, on their hairstyle, etc. Typical decorative cosmetics products are nail polishes, eye shadows, lipsticks, powders—both for the face and the body—hair sprays, and the like. Recently allergic reactions have occurred to the wearers to a very high degree in relation to such compositions, particularly when dyes or carrier materials are used which are suited to act as nutrient media for bacteria and colonization of micro-organisms or which may age due to simple chemical decomposition, e.g. under the effects of light, when the products are allowed to stand for an extended period of time, thus producing decomposition products which may cause allergies.

Another disadvantage of known decorative cosmetic products is their only very restricted period of usefulness and their frequent sensitivity to temperature; this is the reason why storage in specialized cosmetics shops is not unproblematic.

Extensive tests on animals even are not suited to predict undubitably such allergic reactions as those which may be caused particularly by decomposition arising from extended or inadequate storage.

Moreover, there is an ever-increasing demand for particularly lustrous reflecting cosmetic colours for evening events or for the makeup of actors, with the demands to luster and high reflectivity not being satisfied in this field by the common organic dyes or even the normal inorganic minerals.

The problem underlying the present invention is thus the provision of an improved cosmetic composition which will employ dyes which are better to tolerate and afford better optical effects.

According to the present invention, this problem is solved by a composition comprising a liquid, highly viscous or a solid, dermatologically compatible carrier material and a pure powder of precious stones or mixtures of precious stones. If necessary, incinerated precious stones may be used.

The composition may, of course, contain a perfume component as usual in cosmetics.

In a preferred embodiment precious stone powder is added into a carrier liquid in which it is emulsified or emulsifiable, if necessary by means of the addition of emulsion stabilizers. Such liquids are suitable, for instance, for liquid eye shadows, liquid lip gloss, nail polishes and the like.

It has proven to be expedient for other preferred applications to use the inventive composition in a highly viscous salve-like carrier material desirable for applications such as creamy eye shadows, soft lipsticks, creamy lip gloss and similar products. It turned out that eucerine or VASELINE® are specifically well suited as stable carrier materials.

Silicic acid may also be added as an additional auxiliary product.

Another preferred embodiment of the inventive composition is a mixture of precious stone powder with powder bases known per se, such as powdered soapstone or talcum powder. These powders may be used as lustrous makeup or lustrous talcum powder either in a loose or cake form.

The inventive decorative compositions contain the precious stone powder in quantities by up to 10% in weight, preferably by roughly 5% by weight. Depending on the respective application, however, the quantity may also be increased or reduced.

Due to purely mineral crystallized compounds being used as dyes, which are moreover very hard and, due to the missing surface pores, are not suited to form nutrient media for bacteria allergic reactions to these coloring materials may practically be precluded.

Earth or mineral colors such as clays, which have so far been used, are a really ideal nutrient medium for bacteria due to their porous surface.

But organic dyes, too, which are used, for instance, in combination with metal powders for eye shadows, have frequently resulted in allergic reactions to the dyes themselves or to by-products of reactions, which adhered to them.

The following materials have so far proven themselves to be suited as "precious stones", this list, however, not being an exclusive and complete enumeration: sapphire, ruby, emerald, gem topaz, moonstone, cat's eye, zirconium, rock crystal, agate, amethyst, aquamarine, aventurine, amber, beryl, bloodstone, chrysoberyl, chrysoprase, chrysolite, chrysocolla, chalcedony, dioptase, fire opal, fluorite, garnet, oriental topaz, hyacinth, hematite, jade, cornelian, lapis lazuli, labradorite, malachite, nephrite, onyx, opal, obsidian, padparsha, peridot, rhodolite, rhodochrosite, rubellite, blue quartz, sodalite, spinel, sardonyx, tansanite, topaz, tourmaline, tiger's-eye, zoisite, turquoise, Chile-lapis, quartz, smoky quartz, and jasper. Corals and pearls could be expediently employed as well to produce cosmetic compositions with a nacreous luster so that in this context corals and pearls will be referred to as precious stones as well.

Apart from its good compatibility, the inventive decorative cosmetics product is characterized by an extreme purity of colour, brilliance and luster as it is demanded for actors' makeup specifically in the present-day frequent use of lasers on the stage.

The invention will be explained in more detail in the following with reference to examples:

EXAMPLE 1

Powder eye shadow 100 g malachite were crushed in a precious stone mill, a commercially available agate grinder, for 4 hours. The precious stone powder thus obtained had a particle size distribution between 0.0005 and 0.003 millimeters=0.5 to 3 micron. 5 g of the malachite powder were homogeneously kneaded together with 95 g eucerine cum aqua in a kneading machine and the resulting mixture was filled into jars. The result was a very well adhesive, strongly shiny and reflecting green eye shadow.

EXAMPLE 2

10 g lapis were crushed into powder as described in Example 1 above, and kneaded with 90 g VASELINE® in a kneader. The resulting mixture was filled into jars and furnished a lustrous eye shadow of blue color.

EXAMPLE 3

Powder eye shadow 80 g finely powdered talcum, 10 g highly pure silicon dioxide, as well as 10 g of ground turquoise were homogenously intermixed in a mixer. Then the powder mixture was pressed into a powder cake. The result was a turquoise eye shadow of intensive coloring.

EXAMPLE 4

Talcum powder 90 g of powdered soapstone as well as 5 g of crushed corals were homogenously mixed with 5 g of silicon dioxide and filled as loose powder of "angels' skin" coloring.

EXAMPLE 5

10 g of lapis, 10 g of sapphire, 10 g of turquoise and 70 g of azurite powder were homogenously mixed with 100 g VASELINE ® in a kneading machine. The result was an intensively light-blue creamy eye shadow which when filled into jars has a nearly unlimited durability.

I claim:

1. Cosmetic composition, particularly for decorative applications, characterized by a liquid, highly viscous or solid, dermatologically compatible carrier material and a pure powder of precious stones selected from the group consisting of sapphire, ruby, emerald, gem topaz, moonstone, cat's eye, zirconium, rock crystal, agate, amethyst, aquamarine, aventurine, amber, beryl, bloodstone, chrysoberyl, chrysoprase, chrysolite, chrysocolla, chalcedony, dioptase, fire opal, fluorite, garnet, oriental topaz, hyacinth, hematite, jade, cornelian, lapis lazuli, labradorite, malachite, nephrite, onyx, opal, obsidian, padparsha, peridot, rhodolite, rhodochrosite, rubellite, blue quartz, sodalite, spinel, sardonyx, tansanite, topaz, tourmaline, tiger's-eye, zoisite, turquoise, Chile-lapis, quartz, smoky quartz, jasper, corals, pearls and mixtures thereof.

2. Composition according to claim 1, characterized by a precious stone concentration of up to 10% by weight.

3. Composition according to claim 2, characterized by a precious stone concentration of 2-8% by weight.

4. Composition according to claim 2, characterized by a precious stone concentration of 5% by weight.

5. Composition according to claim 1, characterized in that precious stone powders with particle sizes between 0.0005 and 0.003 mm are employed.

6. Composition according to any one of claims 1, 2 or 5, characterized in that the carrier material is liquid, preferably easily drying, with the precious stone powder being emulsified or emulsifiable in the liquid, if necessary by addition of emulsion stabilizers.

7. Composition according to claim 1, characterized in that the carrier material is a dermatologically compatible salve base known per se.

8. Composition according to claim 7, characterized in that the salve base comprises eucerine or VASELINE ®.

9. Composition according to claim 1, characterized in that the carrier material is in powder form.

10. Composition according to claim 9, characterized in that the carrier material is powdered soapstone or gypsum.

11. Composition according to claim 9 or 10, characterized in thst the carrier material is mixed with the precious stone powder and that the mixture is pressed into a cake form.

* * * * *